(12) United States Patent
Davies et al.

(10) Patent No.: US 6,955,462 B1
(45) Date of Patent: Oct. 18, 2005

(54) MIXING CHAMBER

(75) Inventors: Raymond Davies, Cardiff (GB); Kim Dyer, Cardiff (GB); Richard Gunn, Cardiff (GB)

(73) Assignee: Amersham PLC, Amersham (GB)

( * ) Notice: Subject to any disclaimer, the term of this patent is extended or adjusted under 35 U.S.C. 154(b) by 0 days.

(21) Appl. No.: 10/069,694

(22) PCT Filed: Sep. 1, 2000

(86) PCT No.: PCT/GB00/03346

§ 371 (c)(1),
(2), (4) Date: Jul. 15, 2002

(87) PCT Pub. No.: WO01/18539

PCT Pub. Date: Mar. 15, 2001

(30) Foreign Application Priority Data

Sep. 6, 1999 (GB) .................................. 9920924

(51) Int. Cl.⁷ .............................................. B01F 11/00
(52) U.S. Cl. ...................................... 366/258; 366/256
(58) Field of Search .................... 366/118, 256, 258; 422/225; 435/303.3

(56) References Cited

U.S. PATENT DOCUMENTS

| | | | | |
|---|---|---|---|---|
| 181,723 A | * | 8/1876 | Rogers | 366/256 |
| 190,705 A | * | 5/1877 | Clinedinst | 366/256 |
| 292,133 A | * | 1/1884 | Neer | 99/459 |
| 401,863 A | * | 4/1889 | Smith | 366/256 |
| 722,833 A | * | 3/1903 | Furlong | 366/256 |
| 1,254,429 A | * | 1/1918 | Parmeley | 401/4 |
| 1,421,571 A | * | 7/1922 | Rodger | 74/29 |
| 2,088,376 A | * | 7/1937 | Kaskey | 366/256 |
| 2,681,798 A | * | 6/1954 | Muller | 366/118 |
| 2,786,040 A | * | 3/1957 | Dazzi | 524/475 |
| 2,806,679 A | * | 9/1957 | Bruderlin | 366/256 |
| 3,560,162 A | * | 2/1971 | Mittleman | 422/73 |
| 3,589,685 A | * | 6/1971 | Gradishar | 366/260 |
| 4,732,487 A | * | 3/1988 | Pollard | 366/112 |

FOREIGN PATENT DOCUMENTS

| WO | WO 97/15394 A | 5/1997 |
|---|---|---|
| WO | WO 98/08092 A | 2/1998 |

OTHER PUBLICATIONS

Patent Abstracts of Japan vol. 0135, No. 31, Nov. 28, 1989 & JP 01 217879 A (Tokyo Yamaichi Denki KK), Aug. 31, 1989.

* cited by examiner

*Primary Examiner*—David Sorkin
(74) *Attorney, Agent, or Firm*—Yonggang Ji; Royal N. Ronning, Jr.; Stephen G. Ryan

(57) ABSTRACT

An apparatus is provided for mixing and maintaining particulates in liquid suspension, the apparatus comprising a reservoir for holding a fluid containing dispersed particles, a substantially horizontally-disposed mixing plate mounted inside the reservoir, the mixing plate having a plurality of vertical holes extending through the plate, and means for raising and lowering the mixing plate inside the reservoir.

12 Claims, 8 Drawing Sheets

MIXING CHAMBER

The present invention relates to dispensing liquid samples containing particles in liquid suspension. In particular the invention relates to a mixing chamber for mixing and maintaining cells, beads, or other particles in liquid suspension and to a method for mixing and maintaining liquid suspensions of cells, beads, or other particles whilst they are being pipetted by means of a robotic workstation.

It is common in the fields of biochemistry and molecular biology to perform tests in liquid media using particulate samples such as cells and beads. For example, scintillant-containing beads are used in automated high throughput screening assays such as radio-immunoassays, receptor binding assays and enzyme assays. There are numerous publications, which describe such techniques, in which receptors or other binding agents are immobilised onto the surface of the bead, and are used in the quantitation of analytes, the detection of competitive binding, or in the measurement of enzyme activity. Likewise, cells may be grown in liquid suspension and thereafter treated with active agents such as putative or candidate drug molecules for in-vitro drug metabolism, toxicology and drug profiling studies. In order to automate screening assays it is necessary to have a means of dispensing beads, cells or other particulate materials into microwell plates. A number of vendors supply liquid handling instrumentation which can be used to dispense such samples, including dispensers which can simultaneously dispense into 96- and 384-microwell plate formats. However, particulate samples must be maintained in an homogenous suspension to ensure precise dispensing. Conventional apparatus for mixing fluid suspensions of particulate materials rely on a variety of mechanical mixing arrangements. These include the commercially available paddle style mixers and rotary tumble style stirrers.

U.S. Pat. No. 4,812,856 discloses a method and apparatus for dispensing a fluid with dispersed particles using the ink jet principle, the apparatus comprising a reservoir to hold the fluid and dispersed particles and means to agitate the fluid to maintain the dispersed particles in suspension.

The present invention seeks to provide a mixing chamber which is suitable for mixing particulates in liquid suspension and for dispensing homogeneous samples into microwell plates, which is an alternative to current apparatus and methods and which can be used with a range of particulate sizes and types, both biological and non-biological.

According to one aspect of the present invention, there is provided apparatus for mixing and maintaining particulates in liquid suspension, the apparatus comprising a reservoir for holding a fluid containing dispersed particles, the reservoir having an open top, side walls, end walls and a base; a substantially horizontally-disposed mixing plate mounted inside the reservoir, the mixing plate having a plurality of vertical holes extending through the plate; and means for raising and lowering the mixing plate relative to the reservoir.

Suitably, the mixing plate contains an array of holes extending through the plate, the holes being in fixed relationship one with another. Preferably the mixing plate contains an array of 24-, 96- or 384-holes.

The reservoir is mounted inside an outer casing which is adapted to include means for engaging with suspension handles of the mixing plate for raising and lowering the mixing plate inside the reservoir. In a first embodiment of the apparatus according to the invention, means are provided for raising and lowering the mixing plate inside the reservoir, said means comprising at least one piston in contact with the outer casing of the apparatus and operatively connected to an air supply. The air supply to the piston (not shown) is controlled by means of a pressure regulator, solenoids and throttle valve so as to deliver bursts or pulses of air to activate the piston. In a second embodiment of the apparatus, the mixing plate may be raised and lowered by means of a toothed drive wheel into which is set an eccentric peg which engages a slot in the outer casing of the apparatus, the drive wheel being driven through a gear train and drive shaft by electric servo drive motor.

Alternative means for raising and lowering the mixing plate inside the reservoir include a solenoid mechanism, hydraulic pressure activating a piston, or by a magnetic mechanism.

Preferably, the apparatus further comprises means for adding samples in liquid suspension to the reservoir by means of a reagent feed pipe and means for removal or re-circulation of unused liquids from the reservoir by means of an overflow pipe.

In a second aspect, the invention provides a method for mixing and maintaining particulate materials in liquid suspension, using the apparatus as described, the method comprising the steps of introducing a liquid suspension of particulate materials to the mixing chamber reservoir, actuating the mixing plate inside the reservoir so as to mix and maintain the particulate materials in liquid suspension.

Suitably, the particulate materials may be selected from biological or non-biological sources, for example, cells (eukaryotic cells, prokaryotic cells), viral particles, glass beads, scintillant beads (PVT, polystyrene, yttrium silicate, yttrium oxide), magnetic latex beads, chromatography media, controlled pore glass beads, and the like.

In order to clarify the principle and the function of the invention, reference is now made to the accompanying drawings and figures in which.

Figure 1:
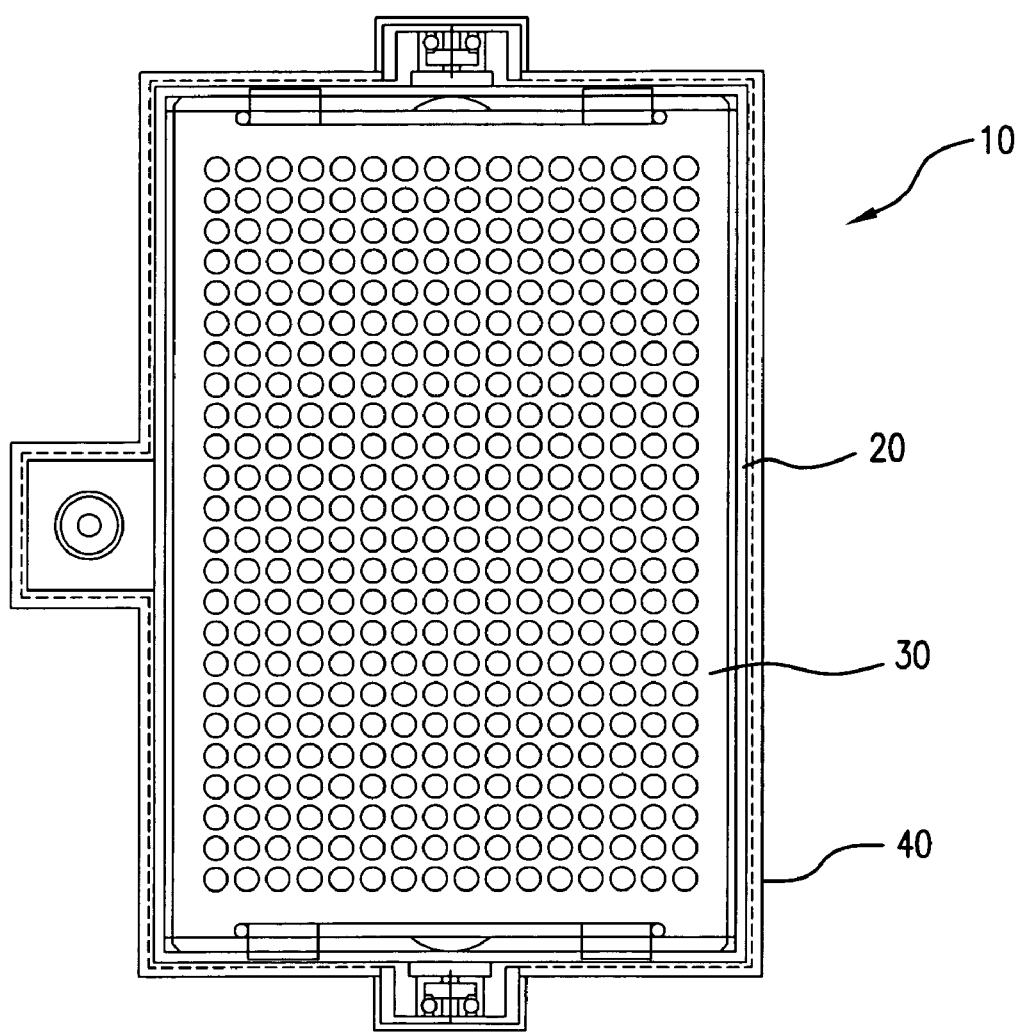
FIG. 1 shows a plan view of the apparatus (10) according to the invention, including the reservoir (20), the mixing plate (30) and the outer casing (40) components of the apparatus.

Referring to FIGS. 1–4 and FIG. 7 of the drawings, the apparatus (10) for mixing and maintaining particulates in liquid suspension includes a reservoir (20) (shown in FIG. 2) for holding a fluid sample containing dispersed particles. The reservoir (20) is rectangular in cross-section, having an open top, side walls (21a, 21b), end walls (22a, 22b), and a base (23). The reservoir (20) is sized to accommodate the substantially horizontally-disposed mixing plate (30) such that there is free vertical movement of the mixing plate within the reservoir (20). Connected vertically to the centre of each end wall (22a, 22b) of the reservoir (20) are linear guide rails (24), each of the linear guide rail mechanisms being supplied with points for holding the outer casing (40) in registry with the reservoir for guiding the outer casing up and down in relation to the reservoir (20).

Figure 2A:
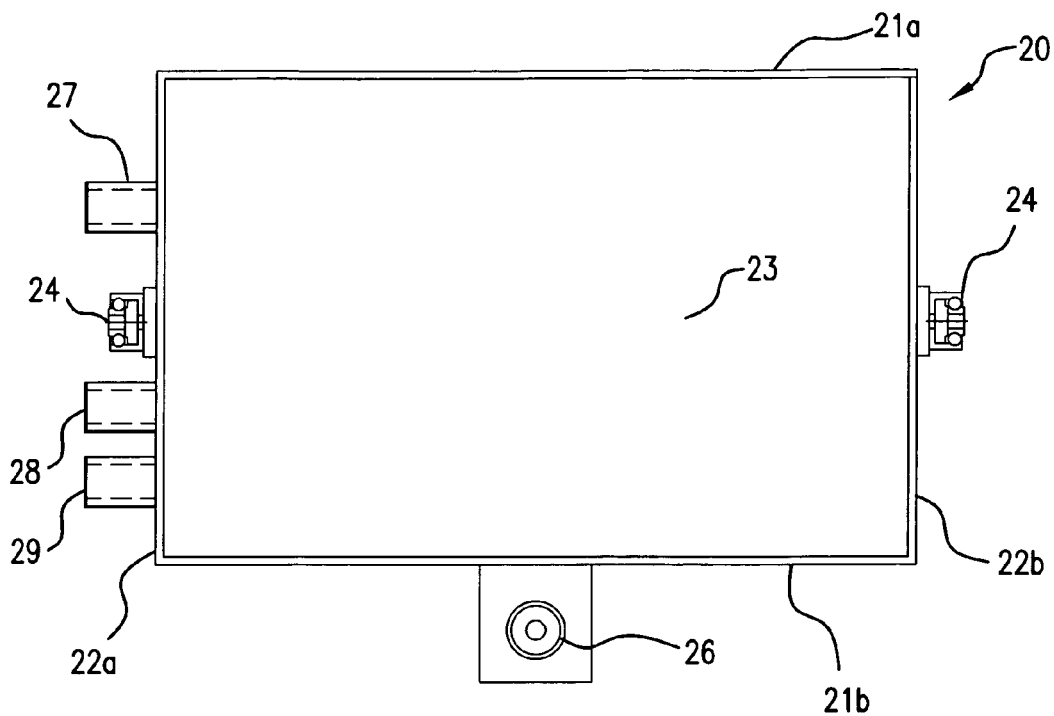
FIG. 2 shows a plan view (FIG. 2a) and side elevations (FIGS. 2b and 2c) of the reservoir (20) according to the invention.
Figure 2B:
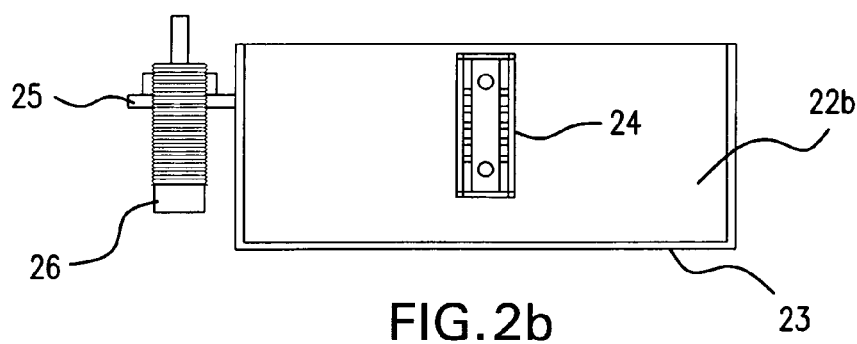
Figure 2C:
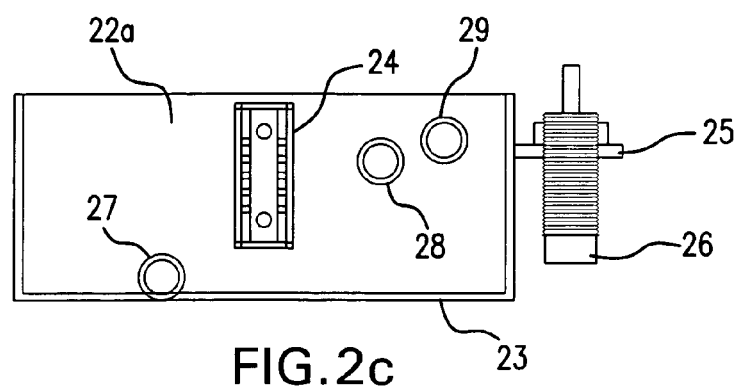

The reservoir shown in FIG. 2 includes a horizontally disposed bracket (25) extending from one side wall (21b). In one preferred embodiment of the apparatus (FIG. 2), a piston (26) is disposed vertically in the horizontally disposed bracket (25). The piston (26) may be positively located to the outer casing by means of a dome-headed locking nut connected to the exposed thread of the piston, in which case retraction of the piston serves to draw the outer casing down over the reservoir in a vertical movement. In the alternative, the piston is not positively connected to the outer casing, in which case, the casing is lowered by gravitational force. In this embodiment of the invention, the piston is actuated so as to raise and lower the outer casing (40) and mixing plate (30) components of the apparatus by means of an air supply. Control of the air supply to actuate the mixing plate is made possible by well-known means. The control of the stroke on the mixing plate is by an electrical timer pulsing a solenoid valve to open at predetermined intervals. The air is throttled to alter the severity of the stroke before outputting to the piston.

Figure 7A:
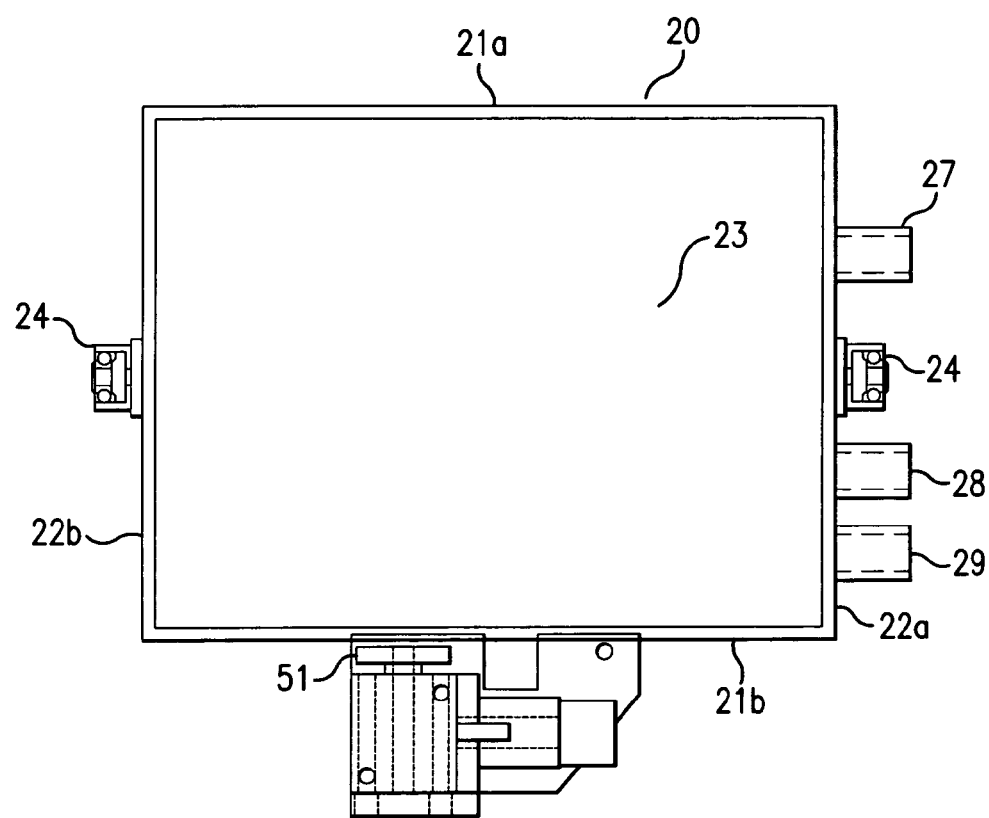
FIG. 7 shows a plan view (FIG. 7a), side elevations (FIGS. 7b and 7c) of an alternative embodiment of the invention.
Figure 7B:
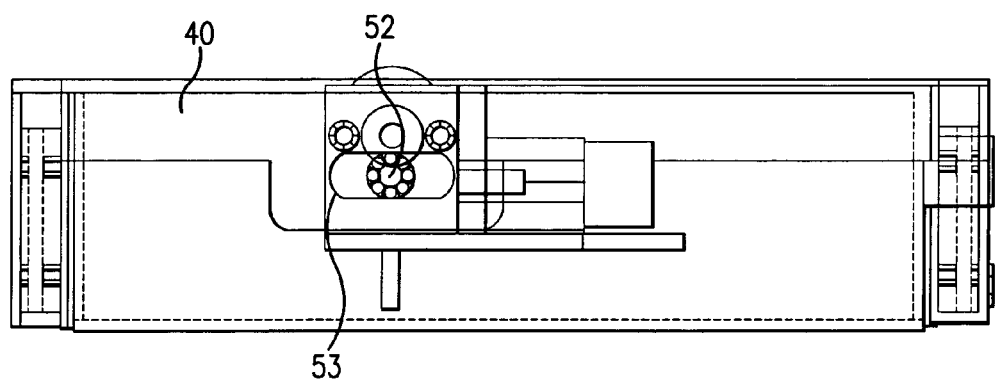
Figure 7C:
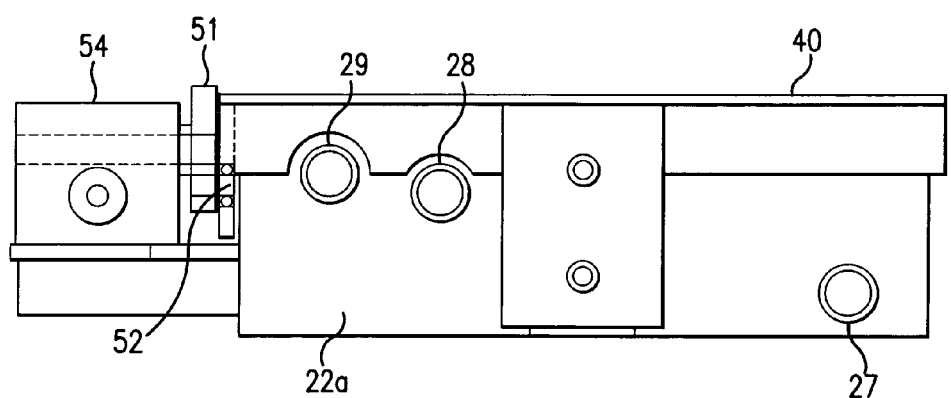

In an alternative embodiment shown in FIG. 7, the mixing plate is raised and lowered by means of a toothed drive wheel (51) into which is set an eccentric peg (52) which engages a slot (53) in the outer casing (40) of the apparatus. The drive wheel is driven through a gear train contained within a detachable housing (54) located on one of the outer side walls (21a or 21b) of the reservoir. In this embodiment, the horizontally disposed bracket (25) and piston (26) are not present. The gear train is driven by means of a drive shaft connected to an electric servo drive motor which is located remote from the apparatus. The servo drive motor may be contained in an enclosure housing a servo drive unit and programmable logic controller controlled by means of an operator interface, so that the mixing plate of the apparatus may be raised and lowered at a predetermined rate which is related to the level of fluid contained in the reservoir.

Alternative means for raising and lowering the mixing plate inside the reservoir include hydraulic pressure activating a piston, or by a solenoid or by magnetic means.

Preferably the apparatus has means for adding particulate materials in liquid suspension to the reservoir through a reagent feed pipe (27) set into the lower portion of one end wall (22a) of the reservoir and means for removal or re-circulation of unused liquid samples from the reservoir through a pipe (28) under the control of an outlet valve (not shown). In use, reagents or wash solutions may be added to the reservoir by means of a syringe connected to the reagent feed pipe, or by means of a peristaltic pump connected to a second reservoir, or by gravity. Reagents may be removed from the reservoir by means of a suction pump connected to the waste pipe. Preferably the apparatus includes an overflow pipe (29) set into either end wall (22a, 22b) of the reservoir (20).

Suitably the reservoir (20) is of a one-piece moulded construction and may be formed from rigid materials, which are resistant to the aqueous, and/or aqueous/organic media used in the dispensing operation. Suitable materials are selected from stainless steel and rigid plastic or polymeric materials. Alternatively, the reservoir may be formed by machining methods in the surface of a plastic or polymeric block. Preferred plastics are selected from polystyrene, polycarbonate, acetal (polyoxymethylene homopolymer or co-polymer), or poly-tetrafluoroethylene (PTFE; Teflon™).

Figure 3A:
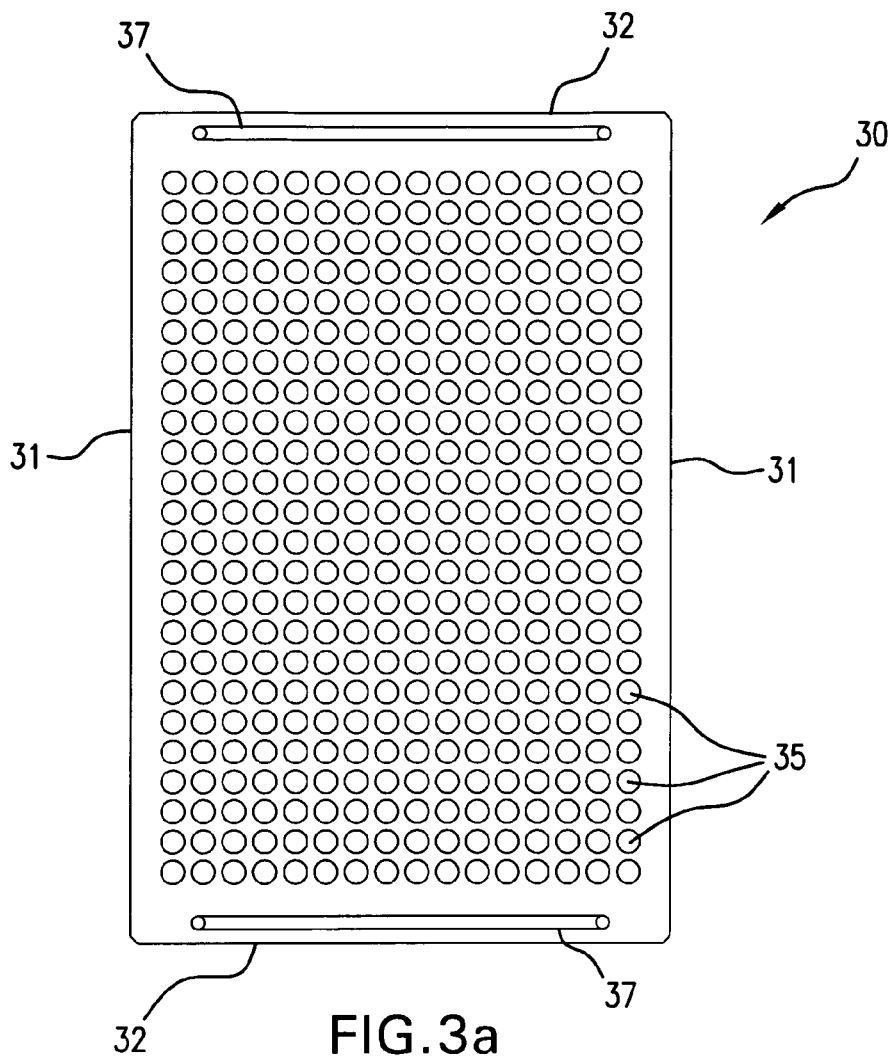
FIG. 3 shows a plan view (FIG. 3a) and side elevation (FIG. 3b) of the mixing plate (30) according to the invention.
Figure 3B:
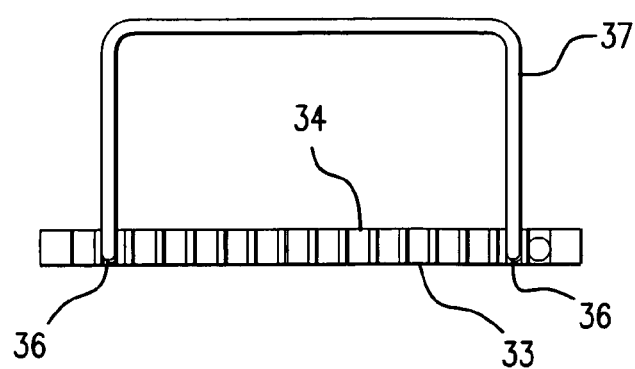

The mixing plate is shown in FIG. 3 and comprises a solid rectangular sheet or block (30) with side walls (31), end walls (32), a base (33) and a top (34), wherein there are formed in the block an array of vertical holes (35) extending through the block from the top surface to the base. As stated previously, the mixing plate is sized to fit inside the reservoir such that there is free vertical movement of the plate within the reservoir (20). Located in holes (36) drilled into the top surface (34) at each end of the mixing plate are suspension handles (37) secured by a friction fit into the holes. The suspension handles are formed from stainless steel and extend upward to connect with lugs located on the outer casing (40) of the apparatus.

Referring to FIG. 3, a 384-hole plate (30) is shown having the dimensions 12.8×8.6×0.5 cm with the 384 holes in an array of 16 rows×24, spaced apart such that the centre of each hole in the plate is precisely located to coincide with the vertical axis of each of the corresponding wells of a 384-well microplate. The mixing plate may be constructed to contain 24-, 96-, or 384-holes as required for dispensing particulate samples into 24-well, 96-well or 384-well microplates. Each of the holes in an array is of substantially the same dimensions and is suitably of a diameter which will allow a pipette tip to be inserted through the hole in the mixing plate into the sample contained in the reservoir. The diameter of each of the holes in the array may be from 2 mm to 7 mm, preferably from 2 mm to 4 mm. The diameter of each of the holes in a 384-hole array is preferably 3 mm. Suitably, the mixing plate is fabricated from a rigid plastic material, preferably acetal (polyoxymethylene homopolymer or co-polymer), or poly-tetrafluoroethylene (PTFE; Teflon™).

Figure 4A:
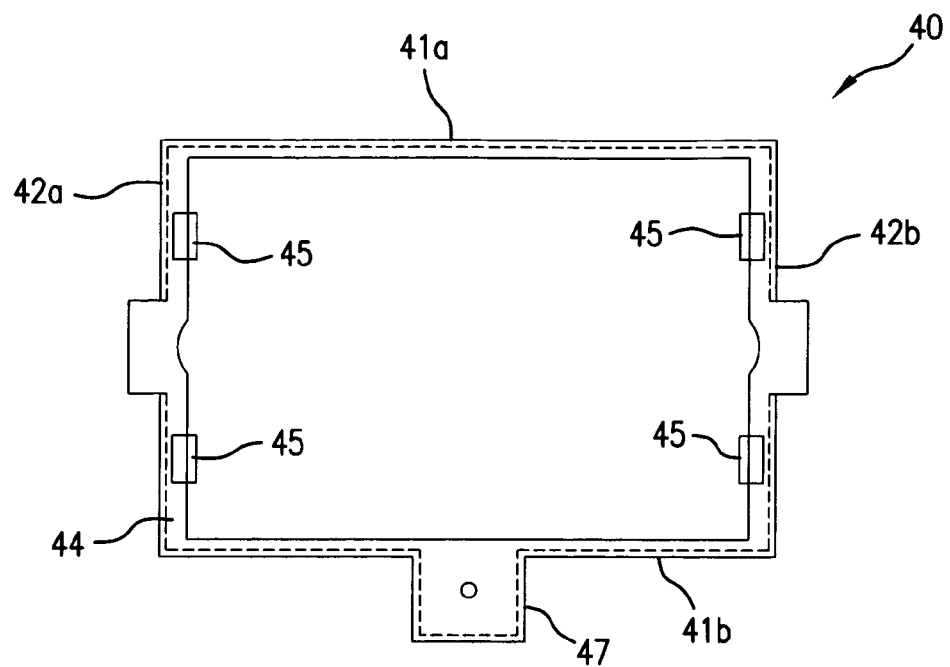
FIG. 4 shows a plan view (FIG. 4a) and side elevations (FIGS. 4b and 4c) of the outer casing (40) according to the invention.
Figure 4B:
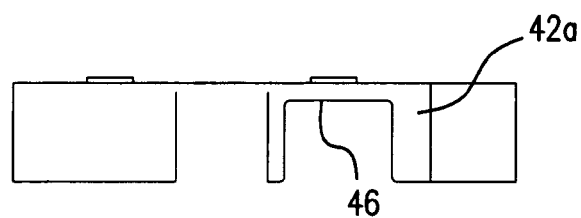
Figure 4C:
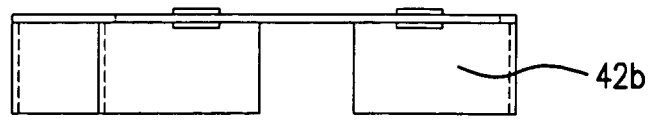

The outer casing (40) of the apparatus is shown in FIG. 4 and is sized to fit over the reservoir (20), including the guide rails (24), and piston (26) (or, alternatively, the gear train housing), while allowing free access of a multi-head pipetter to the sample contained in the reservoir. The outer casing is formed in rectangular cross-section with side walls (41a, 41b), end walls (42a, 42b) and a flange (44) extending horizontally inwards from the vertical walls of the casing. Connected to the flange at each end wall of the casing (40) are lugs (45) suitable for engaging with the suspension handles (37) of the mixing plate (30), for raising the mixing plate. The end walls may include one or more slots (46) to allow reagent and waste feed pipe access to the reservoir (20). Extending horizontally outwards from the side wall (41b) is a bracket (47) to which may be connected inside the piston for upward movement of the casing (40). The casing is mounted over the reservoir and connected to the guide rails (24) by fixing means, such as screws passing through the outer casing in each end wall.

Suitably the outer casing (40) of the apparatus is of moulded construction and may be formed from rigid materials which are resistant to the aqueous and/or aqueous/organic media used in the dispensing operation. Suitably the outer casing is fabricated from stainless steel.

In operation, a liquid suspension of particulates is introduced into the reservoir of the assembled apparatus, by means of the reagent feed pipe. The air supply is switched on to actuate the piston at predetermined intervals, causing the upward movement of the casing and mixing plate, thereby agitating and mixing the particulates in suspension. Upon relaxation of the air pressure the outer casing (and mixing plate) are drawn down (or are allowed to return to their original position under gravity) in readiness for the next cycle. In the alternative embodiment, the mixing plate may be raised and lowered by the toothed drive wheel as described.

By the use of the mixing chamber formed in accordance with the invention and actuating the mixing plate so as to raise and lower the mixing plate, it is possible to mix and maintain particulates in liquid suspension and to remove aliquots of particulate materials in liquid suspension before the materials have had a chance to settle out in the reservoir.

The invention is further illustrated by reference to the following examples.

EXAMPLE 1

An assay to demonstrate maintenance of imaging beads in homogeneous suspension in the mixing chamber Method Streptavidin coated yttrium oxide (YOx) beads (Amersham Pharmacia Biotech) at 20 mg/ml were mixed with [$^3$H]biotin at 0.2 µCi/mg in the mixing chamber for a period of 5 hours. Yttrium oxide beads have a density of 5 g/cm$^3$, which without any means of mixing would settle out of suspension in a few minutes. The mixing chamber was placed on the deck of a Multimek™ 96 (Beckman Coulter) liquid handling device. The Multimek was programmed to remove 96×10 µl and add this to one quadrant of a 384 well microplate, this process was repeated a further three times to fill the remaining three quadrants of the 384 well microplate. The plate was then imaged on LEADseeker™ Homogeneous Imaging System (Amersham Pharmacia Biotech). Plates were dispensed and imaged every 30 minutes throughout the five-hour mixing period.

Results

Figure 5:
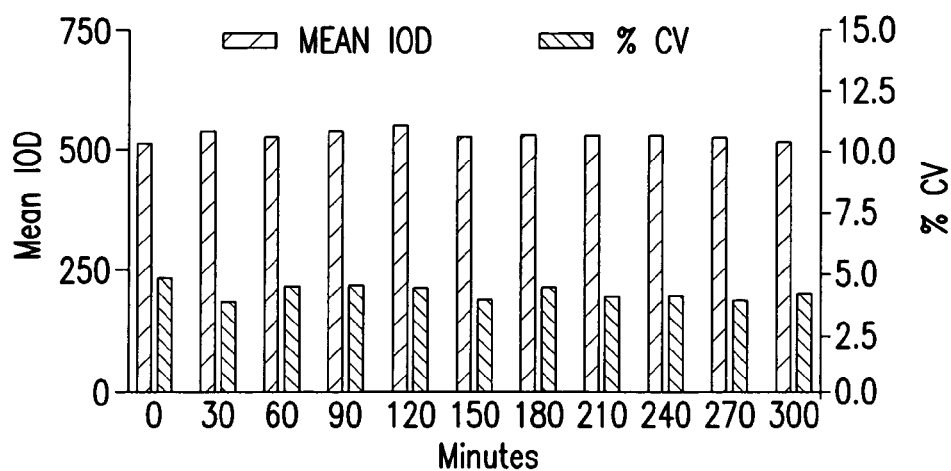
FIG. 5 is a plot demonstrating maintenance of imaging beads in homogeneous suspension in the mixing chamber according to Example 1.

The signal measured from each well is reported as integrated optical density (IOD). The mean IOD across each plate and coefficient of variation (% CV) for each plate were calculated and are shown in FIG. 5. The results showed that the mixing device maintained a homogeneous suspension of YOx beads as demonstrated by the uniform % CV and the uniform mean IOD measured throughout the mixing period.

EXAMPLE 2

An assay to demonstrate mammalian cell viability following dispensing from the mixing chamber Method V-79 cells (Chinese hamster lung, ECACC no. 86041102) were grown in Dulbecco's modified Eagle's minimal essential medium (DMEM), supplemented with 10% (w/v) foetal bovine sera (FBS), 2 mM L-Glutamine, 50 IU/ml Penicillin, 50 µg/ml Streptomycin to sub-confluence at 37° C. in a humidified 5% CO$_2$ incubator. The cells were then re-suspended by treatment with Trypsin-EDTA. Cells were diluted to 5000 cells/ml in culture medium. Cells were mixed in the mixing chamber and 100 µl dispensed into each well of 2×96 well Cytostar-T plates using the Multimek 96. In addition cells were mixed by hand and 100 µl dispensed into each well of a 96 well Cytostar-T plate. Plates were incubated at 37° C. overnight to allow cells to adhere and the following morning [$^{14}$C]thymidine was added to 0.5 µCi/ml.

Plates were counted immediately then incubated at 37° C. Plates were counted again after 5 hours, 19 hours and 24 hours.

Results

Figure 6:
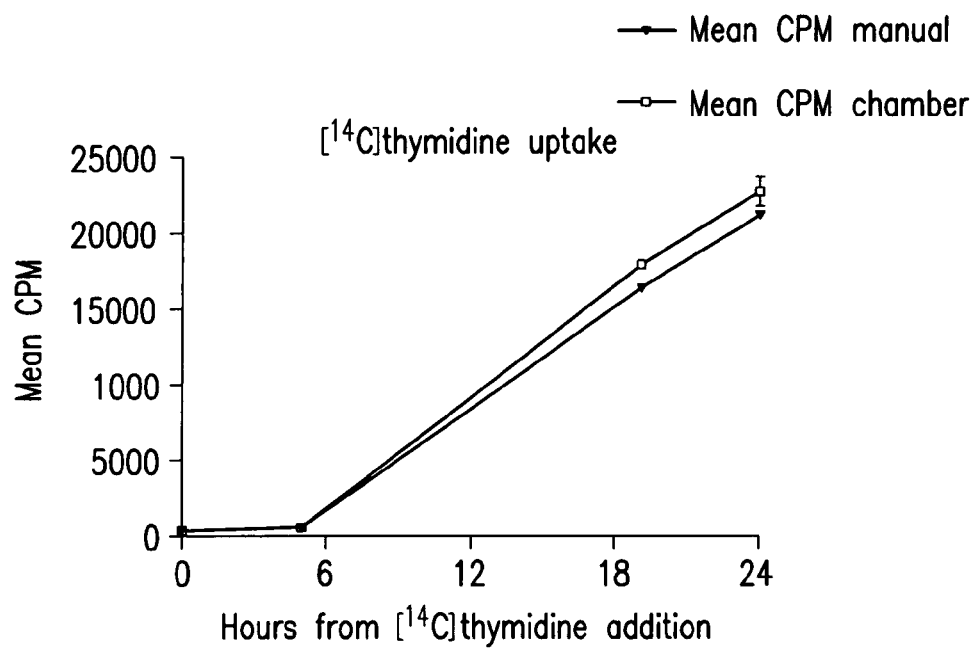
FIG. 6 is a plot demonstrating mammalian cell viability following dispensing from the mixing chamber according to Example 2.

Results obtained on the Microbeta™ (Wallac) are shown in FIG. 6. The [$^{14}$C]thymidine uptake graph displays an increase in mean CPM over time, showing that the V-79 cells were growing and incorporating [$^{14}$C]thymidine, therefore, indicating that they were still viable following mixing. V-79 cells grew equally well whether mixed manually or using the mixing chamber. After 24 hours of growth the % CV across the 96 well microplate was 2.9 for V-79 cells mixed in the chamber and 4.1 for those mixed manually, indicating that the mixing chamber produced a more homogeneous suspension of cells than achieved manually.

What is claimed is:

1. An apparatus for mixing and maintaining particulates in liquid suspension, the apparatus comprising a reservoir for holding a fluid containing dispersed particles, said reservoir mounted inside an outer casing and having an open top, side walls, end walls and a base; a substantially horizontally-disposed mixing plate mounted inside the reservoir, the mixing plate having a plurality of vertical holes extending through the plate; and means for raising and lowering the mixing plate relative to the reservoir; wherein said means for raising and lowering the mixing plate inside the reservoir comprises at least one piston in contact with the outer casing of the apparatus and operatively connected to an air supply.

2. The apparatus as claimed in claim 1 wherein the reservoir further comprises means for adding samples in liquid suspension to the reservoir by means of a reagent feed pipe and means for removal or re-circulation of unused liquids from the reservoir by means of an overflow pipe.

3. The apparatus as claimed in claim 1 wherein the mixing plate contains an array of holes extending through the plate, the holes being in fixed relationship one with another.

4. The apparatus as claimed in claim 3 wherein the mixing plate contains an array of 24-, 96- or 384- holes.

5. A method for mixing and maintaining particulate materials in liquid suspension, using the apparatus according to claim 1, the method comprising the steps of introducing a liquid suspension of particulate materials to the mixing chamber reservoir, actuating the mixing plate inside the reservoir so as to mix and maintain the particulate materials in liquid suspension.

6. The method as claimed in claim 5 wherein the particulate materials are selected from eukaryotic cells, prokaryotic cells, viral particles, glass beads, scintillant beads, magnetic latex beads, chromatography media, and controlled pore glass beads, wherein said scintillant beads are selected from the group consisting of PVT, polystyrene, yttrium silicate, and yttrium oxide.

7. An apparatus for mixing and maintaining particulates in liquid suspension, the apparatus comprising a reservoir for holding a fluid containing dispersed particles, said reservoir mounted inside an outer casing and having an open top, side walls, end walls and a base; a substantially horizontally-disposed mixing plate mounted inside the reservoir, the mixing plate having a plurality of vertical holes extending through the plate; and means for raising and lowering the mixing plate relative to the reservoir; wherein said means for raising and lowering the mixing plate inside the reservoir comprises a toothed drive wheel into which is set an eccentric peg which engages a slot in the outer casing of the apparatus.

8. The apparatus as claimed in claim 7 wherein the reservoir further comprises means for adding samples in liquid suspension to the reservoir by means of a reagent feed pipe and means for removal or re-circulation of unused liquids from the reservoir by means of an overflow pipe.

9. The apparatus as claimed in claim 7 wherein the mixing plate contains an array of holes extending through the plate, the holes being in fixed relationship one with another.

10. The apparatus as claimed in claim 9 wherein the mixing plate contains an array of 24-, 96- or 384- holes.

11. A method for mixing and maintaining particulate materials in liquid suspension, using the apparatus according to claim 7, the method comprising the steps of introducing a liquid suspension of particulate materials to the mixing chamber reservoir, actuating the mixing plate inside the reservoir so as to mix and maintain the particulate materials in liquid suspension.

12. The method as claimed in claim 11 wherein the particulate materials are selected from eukaryotic cells, prokaryotic cells, viral particles, glass beads, scintillant beads, magnetic latex beads, chromatography media, and controlled pore glass beads, wherein said scintillant beads are selected from the group consisting of PVT, polystyrene, yttrium silicate, and yttrium oxide.

* * * * *